United States Patent [19]

Shiau

[11] Patent Number: 5,269,801
[45] Date of Patent: Dec. 14, 1993

[54] DISPOSABLE HAIR INSERTING SET FOR SCALP MINIGRAFT

[76] Inventor: I-Sen Shiau, 1F, No. 1, Alley 17, Lane 111, Sec. 2, Fu-Hsing S. Rd., Taipei City, Taiwan

[21] Appl. No.: 828,152

[22] Filed: Jan. 30, 1992

[51] Int. Cl.⁵ .............................. A61B 17/34
[52] U.S. Cl. .................................... 606/187
[58] Field of Search ............... 606/185, 187, 131, 133; 604/48, 158

[56] References Cited

U.S. PATENT DOCUMENTS 3,699,969 10/1972 Allen .................................. 606/187
4,921,479 5/1990 Grayzel ............................... 604/160

FOREIGN PATENT DOCUMENTS 2512483 3/1983 France ................................. 606/187

Primary Examiner—Stephen C. Pellegrino
Assistant Examiner—William Lewis
Attorney, Agent, or Firm—Longacre & White

[57] ABSTRACT

The minigraft inserting set includes a guiding tube made from a plastic sheet and a pushing stick configured to slide into the guiding tube.

8 Claims, 3 Drawing Sheets

DISPOSABLE HAIR INSERTING SET FOR SCALP MINIGRAFT

BACKGROUND OF THE INVENTION

1. Field of Invention

This invention relates to an inserting set, more particularly to a hair inserting set which can provide more efficient implantation of hair than prior art ones.

2. Description of the Related Art

Recently the art of implanting a minigraft with hair onto a bald scalp on a head has developed in the surgical field. It can be said to be a technical breakthrough in the field of surgery and a great help for baldheaded persons. Of course, to implant a plurality of minigrafts with hairs on a bald scalp, an inserting set must be used. Presently, a forceps is used for implanting minigrafts with hairs, resulting in damage to the hair follicles and the process is tedious, thus causing inconvenience to the operator. In addition, since an incisional slit on the bald scalp is greater than the inserted minigraft, the inserted minigraft (4) occasionally protrudes from the slit after insertion, as can be seen in FIGS. 1 and 2.

SUMMARY OF THE INVENTION

A primary object of the present invention is to provide a minigraft inserting set which can improve the tedious process of inserting minigrafts of hair on a scalp of a baldheaded person.

Another object of the invention is to provide a hair inserting set, the application of which can provide more efficiency in implantation of hair on a bald scalp.

According to the present invention, the hair inserting set includes a guiding tube which is made of a flexible plastic sheet having two longitudinal edges rolled inwardly in such a manner that one edge overlaps the other thereby confining a receiving space therein and a pushing stick which is configured with the receiving space is slidably inserted into the receiving space of the guiding tube.

BRIEF DESCRIPTION OF THE DRAWINGS

Other features and advantages of the present invention will become apparent in the following detailed description, including drawings, all of which show a non-limiting form of the present invention and of which.

DETAILED DESCRIPTION OF THE PREFERRED EMBODIMENT

Figure 1:
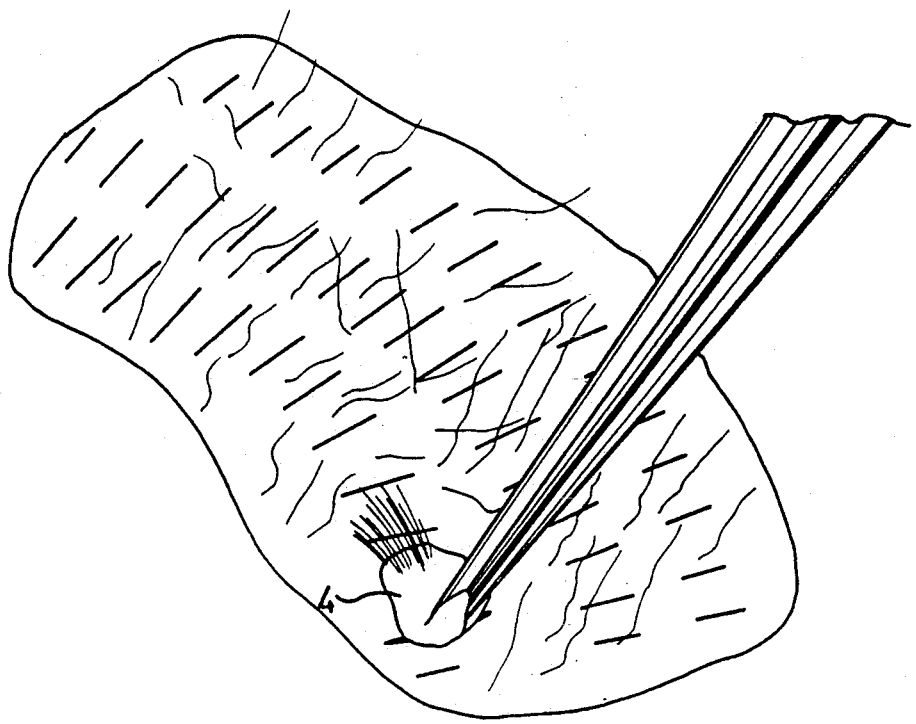
FIG. 1 shows an inserting set of the prior art in application.
Figure 2:
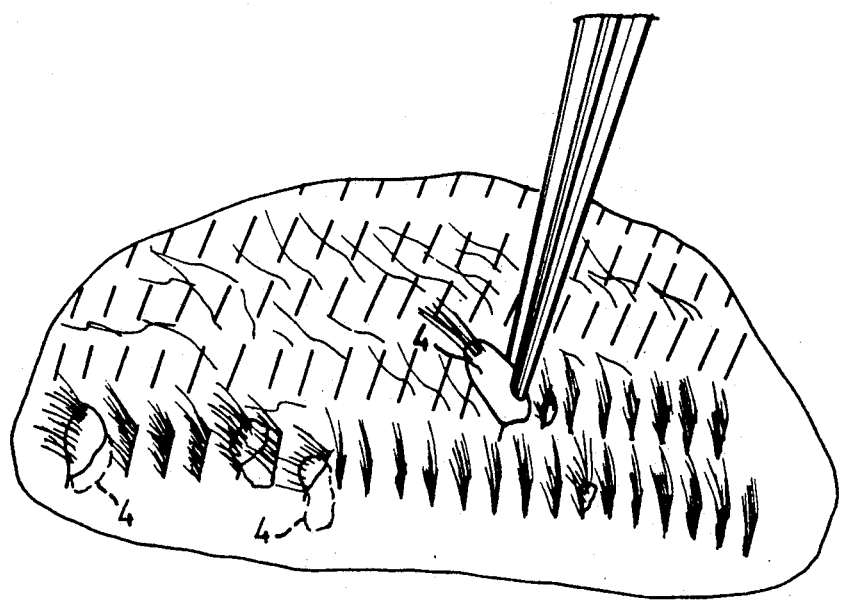
FIG. 2 shows a scalp minigraft inserted by the inserting set of FIG. 1, which scalp minigraft protruding from an incisional slit of a scalp of a baldhead.
Figure 3:
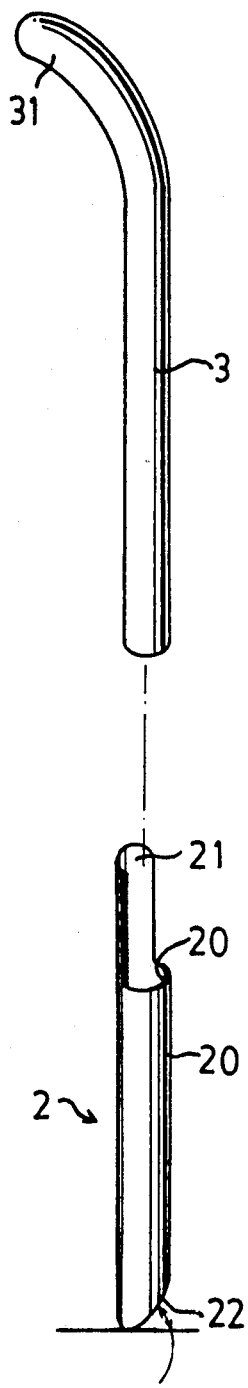
FIG. 3 shows a minigraft inserting set of the present invention.
Figure 4:
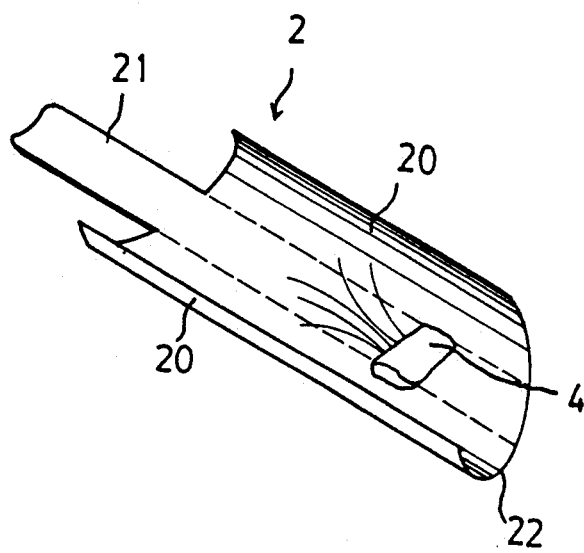
FIG. 4 shows an exploded view of the inserting set of FIG. 3.

Referring to FIGS. 3 and 4, an inserting set (2) for implanting a scalp minigraft of the present invention includes a guiding tube (20) which is made of a flexible plastic sheet, such as polypropylene plastic, and which has two longitudinal edges rolled inwardly in such a manner that one overlaps the other thereby confining a receiving space therein. Folding lines (24) facilitate forming the flexible plastic sheet into a guide tube with an oval-shaped cross section by providing weakened areas along the major axis of the oval-shaped cross section. A pushing stick (3) is slidably inserted into the receiving space. In order for the pushing stick (3) to slide into the receiving space of the guiding tube (20), the pushing stick (3) is configured with the guiding tube. For the pushing facilities, the pushing stick is provided with a hand grip (31) at the top portion.

The guiding tube (20) also has a curved wall projection (21) for holding the same during the working process. In order for the guiding tube (20) to be easily inserted in the scalp head, the guiding tube has an edge substantially inclined at the bottom of the same as shown in FIG. 3. According to experiments, a 20 degree inclination with respect to a horizontal line can provide the best efficiency in implanting the minigraft. In order to form an inclined edge, the bottom end (22) of the plastic sheet is cut to have a circular shape.

The manner in which the minigraft is obtained is a known art and which is not directly concerned with the present invention, therefore, clarification of such is omitted here.

Figure 5:
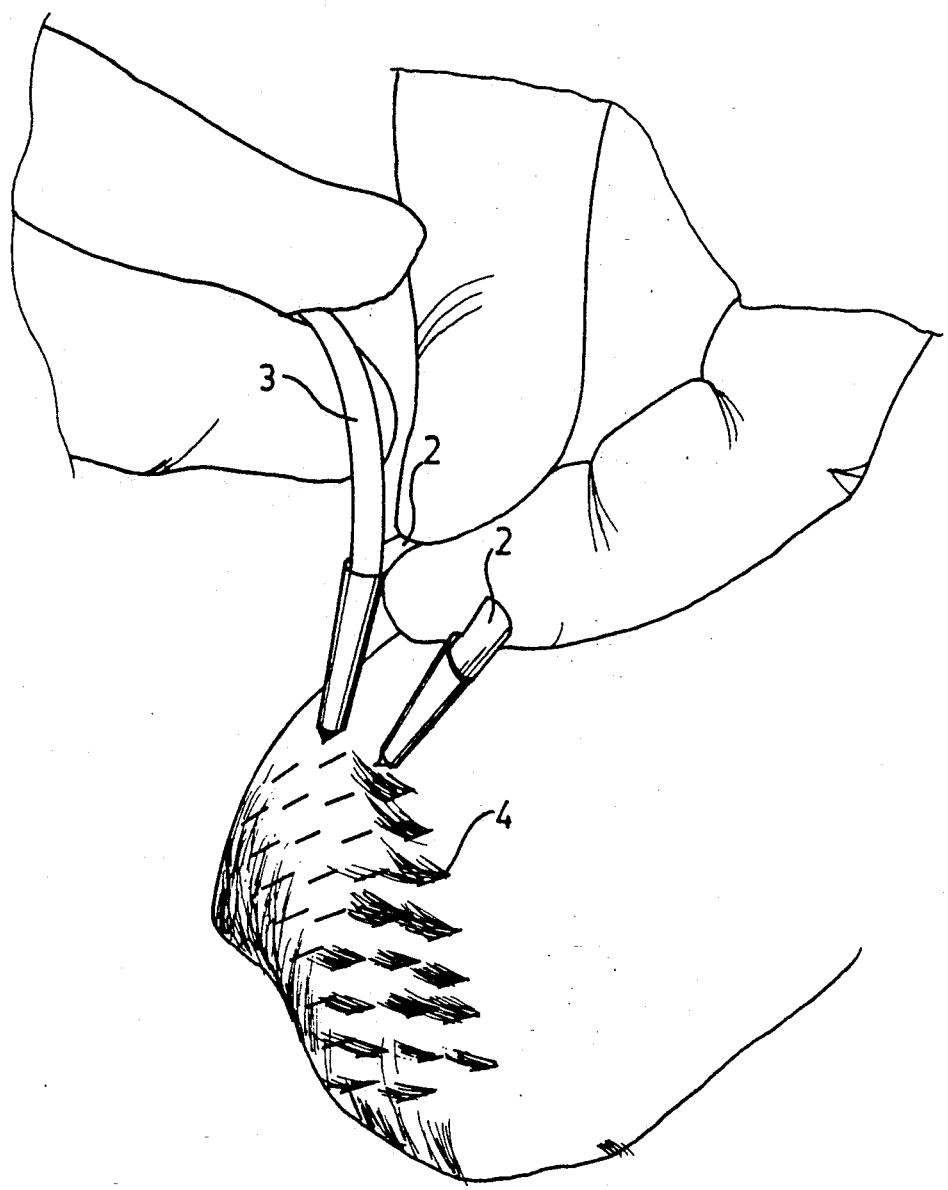
FIG. 5 shows the inserting set of the present invention in application.

The plastic sheet that makes the guiding tube (20) is stretched, as shown in FIG. 4. A scalp minigraft is placed on the plastic sheet, which is then rolled to form said guiding tube. The inclined end (22) of the guiding tube (20) is inserted through an incisional slit (not figured) on the bald head. The pushing rod (3) is slidably inserted into the guiding tube (20), pushing the scalp minigraft (4) deep into the bald scalp as shown in FIG. 5. During the sliding in of the pushing rod, the guiding tube slightly expands outward, enlarging the inclined bottom end of the same. The incisional slit on the scalp head is correspondingly enlarged so that the minigraft can be pushed into the interior of the scalp head through the enlarged incisional slit. When the pushing rod is pulled out from the guiding tube, the guiding tube will retain its initial stage. The enlarged incisional slit also shrinks, thereby closing the same. The inserted minigraft is entrapped underneath the scalp head. Thus the minigraft inserted by the use of the present inserting set will not protrude from the incisional slit as happened in the prior art process. The incisional slits on the bald scalp are prepared in advance before the operation in order to quicken the process.

The application of the present invention can provide the following advantages:

(1) Since the inclined end of the guiding tube can be directly inserted through the incisional slit of the bald scalp, the implantation of the minigraft can be completed within a short time.

(2) Since a pushing stick is used to push the minigraft deep under the bald scalp through the incisional slit, the inserted minigraft will not protrude out as in the processes which use an inserting set of the prior art.

(3) Since no forceps are used in the present process, the follicles are not damaged, which quickens the growth of implanted hair.

(4) Since the inserting set is a disposable one, no contagious disease can be transmitted by the inserting set of the present invention.

(5) Practical tests confirm that the operation which uses the present inserting set takes only ⅕ to ⅓ of the time it normally takes an operation which uses the inserting set of the prior art.

With the invention thus explained, it is obvious to those skilled in the art that several modifications and variations can be made without departing from the scope and spirit of the present invention. It is therefore intended that this invention be limited only in the appended claims.

I claim:

1. A hair inserting set comprising:

a guiding tube being made of a flexible plastic sheet including two longitudinal edges which are rolled inwardly in such a manner that one overlaps the other to define a receiving space therein, said guiding tube further including at least one folding line substantially parallel to said longitudinal edges, said guiding tube having a generally oval-shaped cross section with said at least one folding line located on a major axis of said generally oval-shaped cross section; and an elongated pushing rod slidably inserted into said receiving space of said guiding tube.

2. A hair inserting set as claimed in claim 1, wherein said guiding tube has a lower end which forms an angle with the ground when said guiding tube is placed perpendicularly on the ground.

3. A hair inserting set as claimed in claim 2, wherein said angle is 20 degrees.

4. A hair inserting set as claimed in claim 1, wherein said elongated pushing rod has a top portion which is provided with a hand grip.

5. A hair inserting set as claimed in claim 1, wherein said guiding tube has a curved wall projection extending upward from a top portion of said guiding tube.

6. A hair inserting set comprising:

a flexible sheet including first and second longitudinal edges and a circular edge extending between and connecting said first and second longitudinal edges;

said first longitudinal edge is rolled over and said section longitudinal edge so as to form a guiding tube defining a receiving space therewith having a generally oval cross section, and said circular edge forms a first end of said guiding tube which is oblique with respect to said first and second longitudinal edges; and an elongated pushing rod slidably inserted into said receiving space.

7. The hair inserting set according to claim 6, wherein said first end forms an angle of approximately 20 degrees with respect to said first and second longitudinal edges.

8. The hair inserting set according to claim 6, wherein said flexible sheet further includes a top edge extending between and connecting said first and second longitudinal edges, said top edge having tab means for gripping said guide tube, said tab means extend away from said circular edge.

* * * * *